United States Patent [19]

Tung et al.

[11] Patent Number: 5,654,494

[45] Date of Patent: Aug. 5, 1997

[54] PROCESS FOR THE MANUFACTURE OF 1,1,1,2-TETRAFLUOROETHANE

[75] Inventors: Hsueh Sung Tung, Getzville; Paul Gene Clemmer, Williamsville, both of N.Y.; Gustavo Cerri, Boonton; Yuon Chiu, Denville, both of N.J.; Stanley Michael Jaskot; Nemesio Rogelio Viso, both of Baton Rouge, La.; Addison Miles Smith, Amherst; Jeffrey Warren McKown, East Aurora, both of N.Y.; Jay Philip Friedenson, Randolph, N.J.

[73] Assignee: AlliedSignal Inc., Morris County, N.J.

[21] Appl. No.: 516,669

[22] Filed: Aug. 18, 1995

[51] Int. Cl.$^6$ .................................................. C07C 17/08
[52] U.S. Cl. .................................................. 570/169; 570/168
[58] Field of Search .................................. 570/169, 168

[56] References Cited

U.S. PATENT DOCUMENTS

| | | | |
|---|---|---|---|
| 4,158,675 | 6/1979 | Potter | 260/653.7 |
| 5,243,105 | 9/1993 | Scott et al. | 570/165 |
| 5,243,107 | 9/1993 | Scott et al. | 570/166 |
| 5,334,784 | 8/1994 | Blake et al. | 570/169 |
| 5,334,786 | 8/1994 | Koyama et al. | 570/168 |
| 5,382,722 | 1/1995 | Scott et al. | 570/166 |
| 5,395,996 | 3/1995 | Scott et al. | 570/165 |
| 5,395,998 | 3/1995 | Koyama et al. | 570/168 |
| 5,444,171 | 8/1995 | Ohno et al. | 570/169 |

FOREIGN PATENT DOCUMENTS

| | | |
|---|---|---|
| 0 446 869 | 9/1991 | European Pat. Off. . |
| 0 449 617 | 10/1991 | European Pat. Off. . |
| 0 502 605 | 9/1992 | European Pat. Off. . |

*Primary Examiner*—Alan Siegel
*Attorney, Agent, or Firm*—Jay P. Friedenson

[57] ABSTRACT

This invention relates to a process for producing 1,1,1,2-tetrafluoroethane (HFC-134a). The process reacts, 1,1,1-trifluoro-2-chloroethane (HCFC-133a) and hydrogen fluoride in a first reactor. The product resulting from the first reaction step is brought to a second reactor together with trichloroethylene and hydrogen fluoride. The second reaction is conducted at a higher temperature than the first reactor. Optionally, HCl is removed prior to removal of the crude HFC-134a product. Unreacted HCFC-133a, trichloroethylene and hydrogen fluoride may be recycled back to the first reactor.

20 Claims, 1 Drawing Sheet

PROCESS FOR THE MANUFACTURE OF 1,1,1,2-TETRAFLUOROETHANE

BACKGROUND OF THE INVENTION

1. Field of the Invention

The present invention pertains to a process for the preparation of 1,1,1,2-tetrafluoroethane (HFC-134a). In particular it pertains to a process for the preparation of HFC-134a by a vapor phase catalyzed fluorination of 1,1,1-trifluoro-2-chloroethane (HCFC-133a) with hydrogen fluoride in a first reactor and flowing the resulting product to a second reactor together with trichloroethylene (TCE) and hydrogen fluoride (HF). The second reaction is conducted in the presence of a fluorination catalyst at a higher temperature than the first reaction.

2. Description of the Prior Art

It is known in the art that HFC-134a is a useful compound as a replacement for environmentally disadvantageous chlorofluorocarbon refrigerants. It is also useful as a blowing agent and as an aerosol propellant. Many methods for the production of HFC-134a are known in the art. U.S. Pat. Nos. 5,243,105 and 5,395,996 disclose a method of producing HFC-134a by a two step process which reacts trichloroethylene with hydrogen fluoride to form HCFC-133a. The HCFC-133a is then reacted with hydrogen fluoride in a second reaction to form HFC-134a. In these disclosures, the reaction of trichloroethylene with hydrogen fluoride to form HCFC-133a must be conducted at a lower temperature than the reaction of HCFC-133a with hydrogen fluoride. The reaction sequence and temperature differences are the reverse of those used in the present invention. U.S. Pat. Nos. 5,243,107 and 5,382,722 disclose the reaction of HCFC-133a and HF in a first reaction zone and then passes the reaction product to a second reaction zone together with trichlorethylene. This second reaction zone is at a lower temperature than the first reaction zone. Again, this is the opposite to the temperature difference sequence of the present invention. U.S. Pat. Nos. 5,334,786 and 5,395,998 produce HFC-134a by reacting trichloroethylene and hydrogen fluoride to produce HCFC-133a and then further fluorinate the HCFC-133a. The latter process requires a dilution of the trichloroethylene and hydrogen fluoride with nitrogen or argon gas which is inert to the reaction, and also requires three reactors for this process. U.S. Pat. No. 4,158,675 prepares 1,1,1,2-tetrafluoroethane HFC-134a by a vapor phase catalyzed fluorination of HCFC-133a with hydrogen fluoride in a first reactor. The reaction conditions produce unwanted 1,1-difluoro-2-chloroethylene as an impurity which is reacted with hydrogen fluoride.

It has been a problem in the art to achieve relatively high yields of HFC-134a without causing the simultaneous production of inordinate amounts of by-products which must be treated and disposed of safely. The present invention employs a method wherein intermediate mixtures are recycled through the production steps, thus increasing the efficiency of the process. The higher reactor temperature for the second reaction step affords several advantages. These include higher HCFC-133a productivity and higher TCE conversion. Therefore one can use a smaller reactor and less catalyst. Consequently, operating costs and capital investment are reduced. High conversions of trichloroethylene, approaching 100%, are made possible. Higher TCE conversion can eliminate the possibility of phase separation in the recycle stream. It also reduces amounts of TCE fed to the first reactor, which helps reduce the generation of HCl in the first reactor, and thus raises the equilibrium amounts of HFC-134a product formed in the first reactor. The amount of hydrochlorofluorocarbons as by-products is substantially reduced or eliminated. The process also produces useful HFC-125 and HFC-143a by-products instead of HCFC-123/124 and HCFC-141b/142b, respectively. The HFC-125 and HFC-143a, which are also useful refrigerants, have no ozone-depleting potential whereas HCFC-123/124 and 141b/142b have ozone-depleting potential and are being phased out. Energy is saved because refrigeration is not required to separate crude HFC-134a product from HCFC-133a and hydrogen fluoride that are recycled to the first reactor. In addition, since the reaction of trichloroethylene and hydrogen fluoride is exothermic, heat generated from this reaction is used to keep the second reactor at a higher temperature.

SUMMARY OF THE INVENTION

The invention provides a process for the preparation of 1,1,1,2-tetrafluoroethane which comprises:

a.) conducting a first reaction step comprising vaporizing a first recycled composition comprising hydrogen fluoride and 1,1,1-trifluoro-2-chloroethane at a hydrogen fluoride to 1,1,1-trifluoro-2-chloroethane mole ratio of at least about 1:1, and reacting the composition under suitable conditions in the presence of a fluorination catalyst to thereby form a first reaction product mixture comprising 1,1,1,2-tetrafluoroethane; and b.) conducting a second reaction step comprising vaporizing a second composition comprising hydrogen fluoride, trichloroethylene and the first reaction product mixture from step (a) such that the mole ratio of hydrogen fluoride to trichloroethylene is at least about 3:1 and wherein the second reaction step is conducted in the presence of a fluorination catalyst and at a temperature which is higher than the first reaction step, to thereby form a second reaction product mixture comprising 1,1,1,2-tetrafluoroethane, 1,1,1-trifluoro-2-chloroethane, hydrogen fluoride, trichloroethylene and hydrogen chloride.

In the preferred embodiment, one subsequently recovers 1,1,1,2-tetrafluoroethane. This may be done with the ensuing steps of:

c.) recovering hydrogen chloride by a first distillation from the second reaction product mixture product of step (b);

d.) recovering a product comprising 1,1,1,2-tetrafluoroethane by a second distillation from the mixture resulting from step (c), and obtaining a recycling mixture of 1,1,1-trifluoro-2-chloroethane, trichloroethylene and hydrogen fluoride from the second distillation and adding the recycling mixture as a feed to step (a); and e.) recovering substantially pure 1,1,1,2-tetrafluoroethane from the product of step (d).

Another embodiment of the invention provides optionally adding a portion of the recycling mixture of 1,1,1-trifluoro-2-chloroethane, trichloroethylene and hydrogen fluoride from the second distillation as a feed to the second reaction step (b). Still another embodiment of separating HCl from the first reaction product mixture of the first reactor.

DETAILED DESCRIPTION OF THE PREFERRED EMBODIMENT

Figure 1:
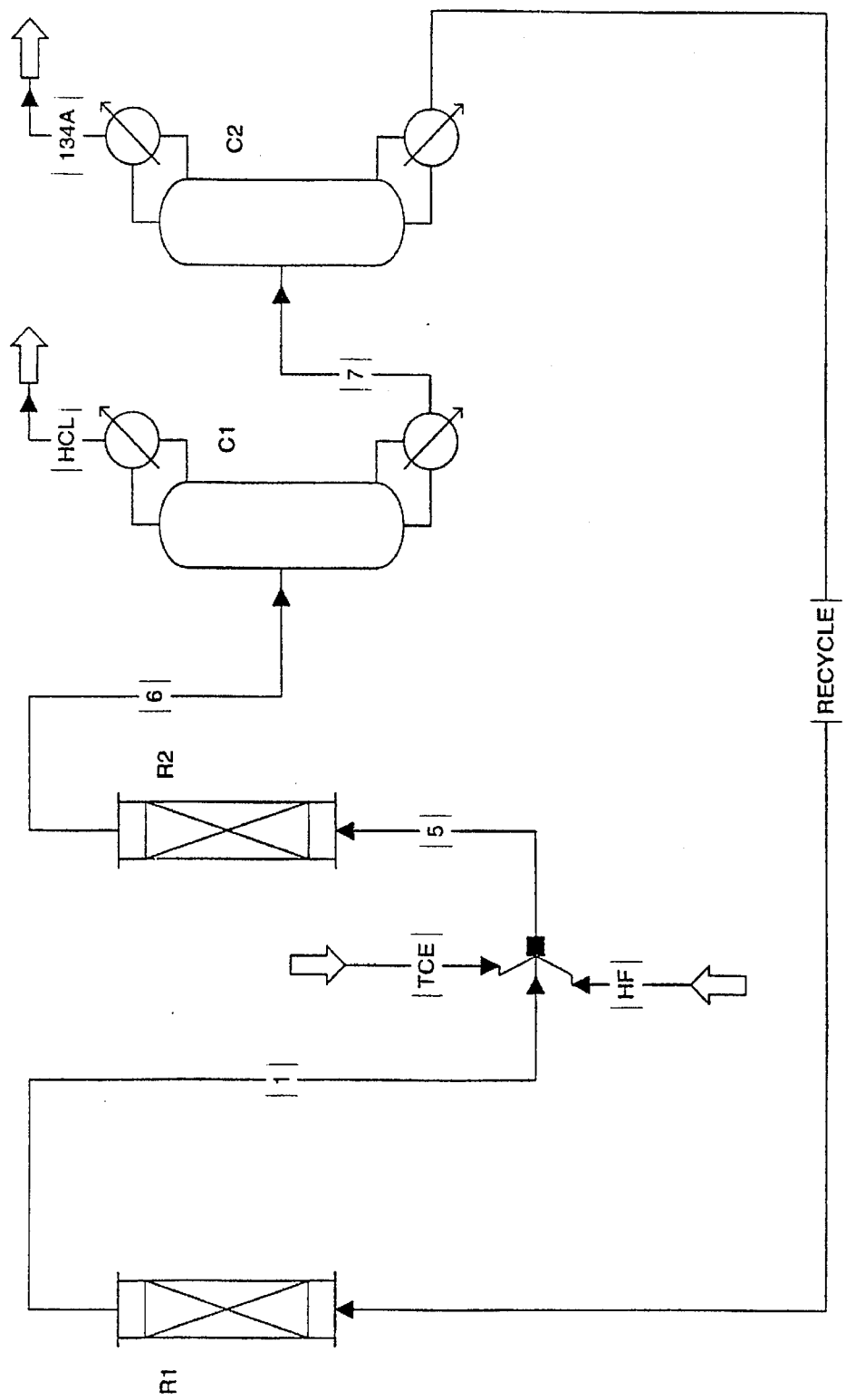
FIG. 1 shows a schematic representation of an equipment arrangement suitable for the invention.

The first step (a) in the production of HFC-134a is vaporizing and reacting a first recycled composition comprising hydrogen fluoride and HCFC-133a in a first reactor. This reactor is shown as R1 in FIG. 1. While fresh hydrogen fluoride and HCFC-133a may be employed here, the process contemplates the composition to contain recycled material from step (b) as hereinafter described. The mole ratio of hydrogen fluoride to HCFC-133a is adjusted to be at least about 1:1, preferably from about 1:1 to about 100:1, more preferably from about 2:1 to about 80:1, and most preferably from about 3:1 to about 60:1. Mole ratios of greater than about 100:1 can be used, however such are less economical. The vaporized composition is preferably heated to a temperature of from about 250° C. to about 425° C., more preferably from about 280° C. to about 400° C. and most preferably from about 300° C. to about 375° C. in the first reactor. The reactor temperature is measured at its outlet end. The pressure of the reactor is not critical. Operating pressure is preferably between about 0 to about 200 psig and still, preferably, from about 50 to about 150 psig. The first reactor is preferably an adiabatic reactor filled with a fluorination catalyst. The organic vapor is allowed to contact the fluorination catalyst for from about 1 to about 100 seconds or more preferably from about 3 to about 70 seconds and most preferably from about 5 to about 60 seconds. For purposes of this invention, contact time is the time required for the gaseous reactants to pass through the catalyst bed assuming that the catalyst bed is 100% void. Any of the fluorination catalysts known in the art may be used. Such fluorination catalysts non-exclusively include chromium, aluminum, cobalt, manganese, nickel and iron oxides, hydroxides, halides, oxyhalides and inorganic salts thereof, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$ and $NiCl_2/AlF_3$. Chromium oxide/aluminum oxide catalysts are described in U.S. Pat. No. 5,155,082 which is incorporated herein by reference. The chromium oxide may be crystalline chromium oxide or amorphous chromium oxide. Amorphous chromium oxide is preferred. Chromium oxide ($Cr_2O_3$) is a commercially available material which may be purchased in a variety of particle sizes. The catalyst is present in the amount necessary to drive the reaction. In the preferred embodiment, small amount of gaseous oxygen or air flows through the chromium oxide to maintain catalyst activity. The amount of air or oxygen supplied to the reactor is preferably from about 0.01 to about 30 mole percent of oxygen relative to the total organics fed to the reactor. A more preferred amount ranges from about 0.05 to about 20 mole percent and most preferably from about 0.1 to about 10 mole percent. The resultant reaction mixture comprises HFC-134a, HCFC-133a, hydrogen fluoride, HCl and small amounts of other by-products.

Step (b) is preferably conducted simultaneously with step (a) and includes vaporizing a second composition comprising hydrogen fluoride, TCE and the first reaction product mixture resulting from step (a) which has been allowed to flow from the first reactor R1 along line 1 to the second reactor R2 as shown in FIG. 1. The HF, TCE and first reaction product mixture resulting from step (a) combine and flow along line 5 to reactor R2 as shown FIG. 1. The process contemplates the composition reacted in step (b) to contain a fresh supply of TCE and HF and optionally recycled material from step (d) as hereinafter described. This second composition is heated to a temperature of about 255° C. to about 430° C., or more preferably from about 285° C. to about 405° C. and most preferably from about 305° C. to about 380° C. Again, the reactor temperature is measured at its outlet end. It is an important feature of the invention that the second reaction step (b) be conducted at a temperature which is higher than that of the first reaction step (a). In the preferred embodiment, the temperature difference between step (a) and step (b) ranges from about 5° C. to about 130° C., or more preferably from about 5° C. to about 60° C. and most preferably from about 5° C. to about 30° C. The pressure of the reactor is not critical. Operating pressure is preferably between about 0 to about 200 psig and still, preferably, from about 50 to about 150 psig. The second reaction step is also conducted in the presence of a fluorination catalyst which may be any of those enumerated as being suitable for the first reaction step (a). The contact time in the second reaction step (b) also may be in the range mentioned above as being suitable for the first reaction step (a). In the second reaction step (b), the reacted mole ratio of HF to TCE may range from about 3:1 to about 100:1, or preferably from about 4:1 to about 90:1 and more preferably from about 5:1 to about 80:1. Mole ratios above 100:1 may be used but are less economical. While the first reaction product mixture is passed to the second reactor in step (b), 1,1,1,2-tetrafluoroethane is made mainly in the first reaction. It then passes through the second reactor. It is contemplated that the non-HFC-134a by-products of the first reaction product mixture may take part in the second reaction. The second reaction product mixture principally produces HCFC-133a and it, together with untreated HF are recycled back to the first reactor where HFC-134a is produced. In the preferred embodiment, for both reaction steps (a) and (b), process flow is in the down direction through the bed of the catalyst. The catalyst is preferably pre-treated and activated as well as regenerated after prolonged use while in place in the reactor. Pre-treatment can be done by heating the catalyst to about 250° C. to about 430° C. in a stream of nitrogen or other inert gas. The catalyst is then activated by treating with a stream of HF diluted with nitrogen gas in order to obtain high catalyst activity. Oxygen is preferably continuously fed to each reactor during production to maintain catalyst activity. Oxygen is fed at a rate sufficient to provide an oxygen to organics mole ratio of from about 0 to about 0.1 or preferably from about 0.005 to about 0.05. If the catalyst is de-activated, it can be regenerated by heating to about 250° C. to about 430° C. in a stream of nitrogen containing a low concentration of oxygen, followed by cooling. Each of the reaction steps (a) and (b) may be conducted in any suitable reaction vessel but it should be constructed from materials which are resistant to the corrosive effects of hydrogen fluoride such as Hastalloy, Inconel and Monel.

The next step (c) in the process recovers hydrogen chloride by a first distillation from the second reaction product mixture product of step (b). The second reaction product mixture flows along line 6 and is subjected to such a distillation by column C1 as shown in FIG. 1, to form a distillate portion and a bottoms portion. The purpose of the distillation is to separate hydrogen chloride from the balance of the second reaction product mixture components. This is done using a standard distillation column in a method well known to one skilled in the art. The distillation is preferably conducted at a pressure which ranges from about 5 psig to about 500 psig, preferably from about 10 to about 400 psig and most preferably from about 50 to about 300 psig. The pressure of the distillation column inherently determines the distillation operating temperature. The distillate portion includes substantially all the hydrogen chloride and the bottoms portion includes the balance of the second reaction product mixture components. The bottoms is then subjected to a second distillation by exiting line 7 and flowing to column C2 as shown in FIG. 1.

Step (d) requires recovering a product of step (c) comprising HFC-134a also by a standard distillation column in a method well known to one skilled in the art such as listed above to form a distillate and a bottoms mixture. The distillate comprises substantially all of the HFC-134a product plus other useful hydrofluorocarbon by-products such as HFC-125 and HFC-143a. The HCFC-133a, hydrogen fluoride and TCE bottoms mixture is recycled back to step (a) as shown by the recycle line of FIG. 1. Step (e) recovers a composition comprising substantially pure HFC134a from the product of step (d) and the other useful hydrofluorocarbon by-products such as HFC-125 and HFC-143a. This is done by standard distillation or other known separation techniques.

The following non-limiting examples are prospective and represent standard process simulation and physical property prediction procedures and the examples serve to illustrate the invention.

EXAMPLES 1–3

These examples demonstrate the effect of temperature on productivity and conversion. In three different experiments, a TCE and HCFC-133a mixture was fed to a packed bed, isothermal reactor at 260° C., 320° C., and 360° C., respectively. The reactor was packed with chrome oxide catalyst. The mole ratio of HCFC-133a to TCE was about 3.3. HF was fed in separately. The mole ratio of HF to TCE was about 13. Air was co-fed at 1.4 mole % $O_2$/organics mole ratio. Reactor pressure was 200 psig. Organics and HF feed rates were adjusted to give the desired contact times of 20, 10, and 5 seconds, respectively. The results are listed below:

TABLE I

| Example | Temp. °C. | Contact Time seconds | (%) TCE Conversion | Productivity (lbs/hr/ft$^3$) HCFC-133a | HFC143a |
|---|---|---|---|---|---|
| 1 | 260 | 20 | 54.9 | 17.8 | <0.1 |
| 2 | 320 | 10 | 59.8 | 23.9 | 3.4 |
| 3 | 360 | 5 | 99.5 | 80 | 15 |

Example 3 is calculated using a reaction kinetic model which was derived from experimental data. These data show the higher the reaction temperature of the second reactor, the higher the TCE conversion, and the higher the HCFC-133a productivities.

EXAMPLES 4, 5 and COMPARATIVE EXAMPLE 6

These examples are to demonstrate the effect of higher temperature in the second reactor on TCE conversion, 133a productivity and useful by-product formation using an integrated system shown in FIG. 1. Examples 4 and 5 were conducted in adiabatic reactors packed with chrome oxide catalyst. TCE and HF were fed to the second reactor (R2) as shown in FIG. 1. HCl is taken off from the HCl column and the heavy cut, consisting of 134a/HF/TCE/133a and other by-products were fed to the crude 134a distillation column where 134a/125/143a/124 were taken off and 133a/HF/TCE were recycled to the first reactor as indicated in FIG. 1. The reaction conditions and parameters are listed in Table 2, with TCE conversion, 133a productivity and amounts of useful by-product formation:

TABLE 2

| Example | 4 | 5 | Comp. 6 |
|---|---|---|---|
| R1 outlet temperature (°C.) | 329 | 333 | 350 |
| R2 outlet temperature (°C.) | 341 | 361 | 260 |
| Pressure (psig) | 60 | 60 | 60 |
| Contact Time in R1 (seconds) | 9 | 9 | 9 |
| Contact Time in R1 (seconds) | 9 | 9 | 9 |
| HF/133a mole ratio in R1 | 14 | 14 | 14 |
| HF/133a mole ratio in R2 | 12 | 12 | 12 |
| HF/TCE mole ratio in R2 | 43 | 43 | 58 |
| TCE conversion in R2 (mole %) | >99% | >99% | 29% |
| 133a productivity in R2 (lbs/hr/ft$^3$) | 7 | 7 | 1.4 |
| Useful by-products: | | | |
| wt % HFC-125 in HFC-134a | 0.11 | 0.89 | — |
| wt % HFC-143 in HFC-134a | 0.007 | 0.16 | — |
| Recycle composition (wt % major components) | | | |
| HF | 65% | 65% | 70% |
| TCE | <0.1% | <0.1% | <6% |
| 133a | 33% | 31% | 23% |

Data of comparative Example 6 are generated for comparable conditions using computer simulation which was derived based on numerous experimental and production data. As indicated in the present invention and shown in the above examples, higher TCE conversion, and higher 133a productivity were obtained when the second reactor (R2) was run at a higher temperature than the first reactor (R1). The TCE concentration was about 0 in the recycle, compared to 6% (about 19% based on total organics). Useful HFC by-product formation was also evident.

EXAMPLE 7

This example demonstrates the energy savings for separating HCl before recovering crude HFC-134a from HCFC-133a and HF that is recycled to the first reactor.

The condensing equipment of the recycle column used to separate the crude HFC134a from the HCFC-133a and HF recycle to the reactor was calculated using a distillation model derived from theory and laboratory measurements of component vapor-liquid equilibrium. The calculation showed that when the HCl co-produced in the reaction is removed together with HFC-134a in the recycle column, the condensing temperature is very low so that refrigeration is required to produce reflux in this column. However, when the HCl is removed first, according to the present invention, the need for refrigeration to produce reflux in the recycle column can be eliminated, thus saving the capital cost of the refrigeration system as well as the cost of energy to operate it. An additional operating energy cost of about 350 HP per metric ton of HFC-134a product are required when HFC-134a and HCL are separated together from HCFC-133a and HF at a normal operating pressure of 150 psig. No refrigeration is required in the recycle column when the HCl is removed first. The energy savings are even greater if the reactors are operated at lower pressure.

What is claimed is:

1. A process for the preparation of 1,1,1,2-tetrafluoroethane which comprises:

a.) conducting a first reaction step comprising vaporizing a first recycled composition comprising hydrogen fluoride and 1,1,1-trifluoro-2-chloroethane at a hydrogen fluoride to 1,1,1-trifluoro-2-chloroethane mole ratio of at least about 1:1, and reacting the composition under suitable conditions in the presence of a fluorination catalyst to thereby form a first reaction product mixture comprising 1,1,1,2-tetrafluoroethane; and b.) conducting a second reaction step comprising vaporizing a second composition comprising hydrogen fluoride, trichloroethylene and the first reaction product mixture from step (a) such that the mole ratio of hydrogen fluoride to trichloroethylene is at least about 3:1 and wherein the second reaction step is conducted in the presence of a fluorination catalyst and at a temperature which is higher than the first reaction step, to thereby form a second reaction product mixture comprising 1,1,1,2-tetrafluoroethane, 1,1,1-trifluoro-2-chloroethane, hydrogen fluoride, trichloroethylene and hydrogen chloride.

2. The process of claim 1 further comprising the subsequent step of recovering 1,1,1,2-tetrafluoroethane.

3. The process of claim 1 further comprising the subsequent steps of:

c.) recovering hydrogen chloride by a first distillation from the second reaction product mixture product of step (b);

d.) recovering a product comprising 1,1,1,2-tetrafluoroethane by a second distillation from the mixture resulting from step (c), and obtaining a recycling mixture of 1,1,1-trifluoro-2-chloroethane, trichloroethylene and hydrogen fluoride from the second distillation and adding the recycling mixture as a feed to step (a); and e.) recovering substantially pure 1,1,1,2-tetrafluoroethane from the product of step (d).

4. The process of claim 1 wherein the first reaction step (a) is conducted at a temperature ranging from about 250° C. to about 425° C.

5. The process of claim 1 wherein the second reaction step (b) is conducted at a temperature ranging from about 255° C. to about 430° C.

6. The process of claim 1 wherein the second reaction step (b) is conducted at a temperature which is at least about 5° C. higher than first reaction step (a).

7. The process of claim 1 wherein the second reaction step (b) is conducted at a temperature which is from about 5° C. to about 130° C. higher than first reaction step (a).

8. The process of claim 1 wherein the second reaction step (b) is conducted at a temperature which is from about 5° C. to about 60° C. higher than first reaction step (a).

9. The process of claim 1 wherein the second reaction step (b) is conducted at a temperature which is from about 5° C. to about 30° C. higher than first reaction step (a).

10. The process of claim 3 further comprising adding a portion of the recycling mixture of 1,1,1-trifluoro-2-chloroethane, trichloroethylene and hydrogen fluoride from the second distillation as a feed to the second reaction step (b).

11. The process of claim 1 comprising the further step of removing HCl from the first reaction product mixture prior to step (b).

12. The process of claim 1 wherein the fluorination catalyst used in steps (a) and (b) is selected from the group consisting chromium, aluminum, cobalt, manganese, nickel and iron oxides, hydroxides, halides, oxyhalides and inorganic salts thereof, $Cr_2O_3/Al_2O_3$, $Cr_2O_3/AlF_3$, $Cr_2O_3/$ carbon, $CoCl_2/Cr_2O_3/Al_2O_3$, $NiCl_2/Cr_2O_3/Al_2O_3$, $CoCl_2/AlF_3$ and $NiCl_2/AlF_3$.

13. The process of claim 1 wherein the fluorination catalyst used in steps (a) and (b) is $Cr_2O_3$.

14. The process of claim 1 wherein the fluorination catalyst used in steps (a) and (b) is $Cr_2O_3$ whose activity is maintained with a stream of oxygen.

15. The process of claim 1 wherein the contact time for the first and second compositions with the fluorination catalyst in steps (a) and (b) ranges from about 1 second to about 100 seconds.

16. The process of claim 1 wherein steps (a) and (b) are conducted at about 50–150 psig.

17. The process of claim 1 wherein the mole ratio of hydrogen fluoride to 1,1,1-trifluoro-2-chloroethane in step (a) ranges from about 1:1 to about 100:1.

18. The process of claim 1 wherein the mole ratio of hydrogen fluoride to trichloroethylene in the second reaction step (b), ranges from about 3:1 to about 100:1.

19. The process of claim 1 wherein the first reaction step (a) is conducted at a temperature ranging from about 250° C. to about 425° C.; the second reaction step (b) is conducted at a temperature ranging from about 255° C. to about 430° C.; the second reaction step (b) is conducted at a temperature which is at least about 5° C. higher than first reaction step (a); the fluorination catalyst used in steps (a) and (b) is selected from the group consisting chromium, aluminum, cobalt, manganese, nickel and iron oxides, hydroxides, halides, oxyhalides and inorganic salts thereof, $Cr_2O_3/Al_2O_3$, $Cr_2O_3/AlF_3$, $Cr_2O_3/$carbon, $CoCl_2/Cr_2O_3/Al_2O_3$, $NiCl_2/Cr_2O_3/Al_2O_3$, $CoCl_2/AlF_3$ and $NiCl_2/AlF_3$; the contact time for the first and second compositions with the fluorination catalyst in steps (a) and (b) ranges from about 1 second to about 100 seconds; steps (a) and (b) are conducted at about 50–150 psig; the mole ratio of hydrogen fluoride to 1,1,1-trifluoro-2-chloroethane in step (a) ranges from about 1:1 to about 100:1; and the mole ratio of hydrogen fluoride to trichloroethylene in the second reaction step (b) ranges from about 3:1 to about 100:1.

20. The process of claim 1 wherein the first reaction step (a) is conducted at a temperature ranging from about 300° C. to about 375° C.; the second reaction step (b) is conducted at a temperature ranging from about 305 ° C. to about 380° C.; the second reaction step (b) is conducted at a temperature which ranges from about 5° C. to about 30° C. higher than first reaction step (a); the fluorination catalyst used in steps (a) and (b) is $Cr_2O_3$ whose activity is maintained with a stream of oxygen; the contact time for the first and second compositions with the fluorination catalyst in steps (a) and (b) ranges from about 5 seconds to about 60 seconds; steps (a) and (b) are conducted at about 50–150 psig; the mole ratio of hydrogen fluoride to 1,1,1-trifluoro-2-chloroethane in step (a) ranges from about 3:1 to about 60:1; and the mole ratio of hydrogen fluoride to trichloroethylene in the second reaction step (b) ranges from about 5:1 to about 80:1.

* * * * *